United States Patent
Uhlrich et al.

(10) Patent No.: US 10,368,897 B2
(45) Date of Patent: Aug. 6, 2019

(54) ULTRASONIC SURGICAL INSTRUMENT

(71) Applicant: COVIDIEN LP, Mansfield, MA (US)

(72) Inventors: Scott D. Uhlrich, Fort Collins, CO (US); Anthony B. Ross, Boulder, CO (US); Robert B. Stoddard, Steamboat Springs, CO (US); Eric R. Larson, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 248 days.

(21) Appl. No.: 15/428,686

(22) Filed: Feb. 9, 2017

(65) Prior Publication Data

US 2018/0221048 A1 Aug. 9, 2018

(51) Int. Cl.
*A61B 17/32* (2006.01)
*A61B 17/00* (2006.01)
*A61B 17/29* (2006.01)

(52) U.S. Cl.
CPC ............. *A61B 17/320092* (2013.01); *A61B 2017/00353* (2013.01); *A61B 2017/2944* (2013.01); *A61B 2017/32007* (2017.08); *A61B 2017/320078* (2017.08); *A61B 2017/320084* (2013.01); *A61B 2017/320094* (2017.08)

(58) Field of Classification Search
CPC ......... A61B 2017/32007; A61B 2017/320094; A61B 2017/320078; A61B 2017/320084; A61B 2017/2944; A61B 17/320092
See application file for complete search history.

(56) References Cited

U.S. PATENT DOCUMENTS

| | | |
|---|---|---|
| 4,063,557 A | 12/1977 | Wuchinich et al. |
| 4,223,676 A | 9/1980 | Wuchinich et al. |
| 4,526,571 A | 7/1985 | Wuchinich |
| 4,750,488 A | 6/1988 | Wuchinich et al. |
| 5,176,677 A | 1/1993 | Wuchinich |
| 7,479,148 B2 | 1/2009 | Beaupre |
| 7,846,155 B2 | 12/2010 | Houser et al. |
| 8,348,880 B2 | 1/2013 | Messerly et al. |
| 8,663,270 B2 * | 3/2014 | Donnigan .............. A61B 17/29 227/60 |
| 2005/0033337 A1 | 2/2005 | Muir et al. |
| 2005/0192610 A1 | 9/2005 | Houser et al. |
| 2007/0173872 A1 | 7/2007 | Neuenfeldt |
| 2007/0282333 A1 | 12/2007 | Fortson et al. |
| 2010/0063525 A1 | 3/2010 | Beaupre et al. |

(Continued)

*Primary Examiner* — Tuan V Nguyen

(57) ABSTRACT

An ultrasonic surgical instrument is provided, including a handpiece, a lever operably coupled to the handpiece and movable between first, second, and third positions, a shaft assembly extending distally from the handpiece, and an ultrasonic waveguide extending through the shaft assembly and defining a fixed jaw member at a distal end portion thereof. An outlet at the distal end of the fixed jaw member provides irrigation of fluid. The waveguide functions as an aspirator well as a transector/dissector of tissue. A movable jaw member is disposed towards a distal end portion of the shaft assembly and is operably coupled to the lever such that movement of the lever between the first, second, and third positions moves the movable jaw member relative to the fixed jaw member between a retracted position, an extended open position, and an extended closed position.

20 Claims, 6 Drawing Sheets

(56) References Cited

U.S. PATENT DOCUMENTS

2013/0131705 A1\* 5/2013 Akagane .......... A61B 17/32006
606/169
2014/0100600 A1\* 4/2014 Kendrick ............... A61B 17/29
606/205

\* cited by examiner

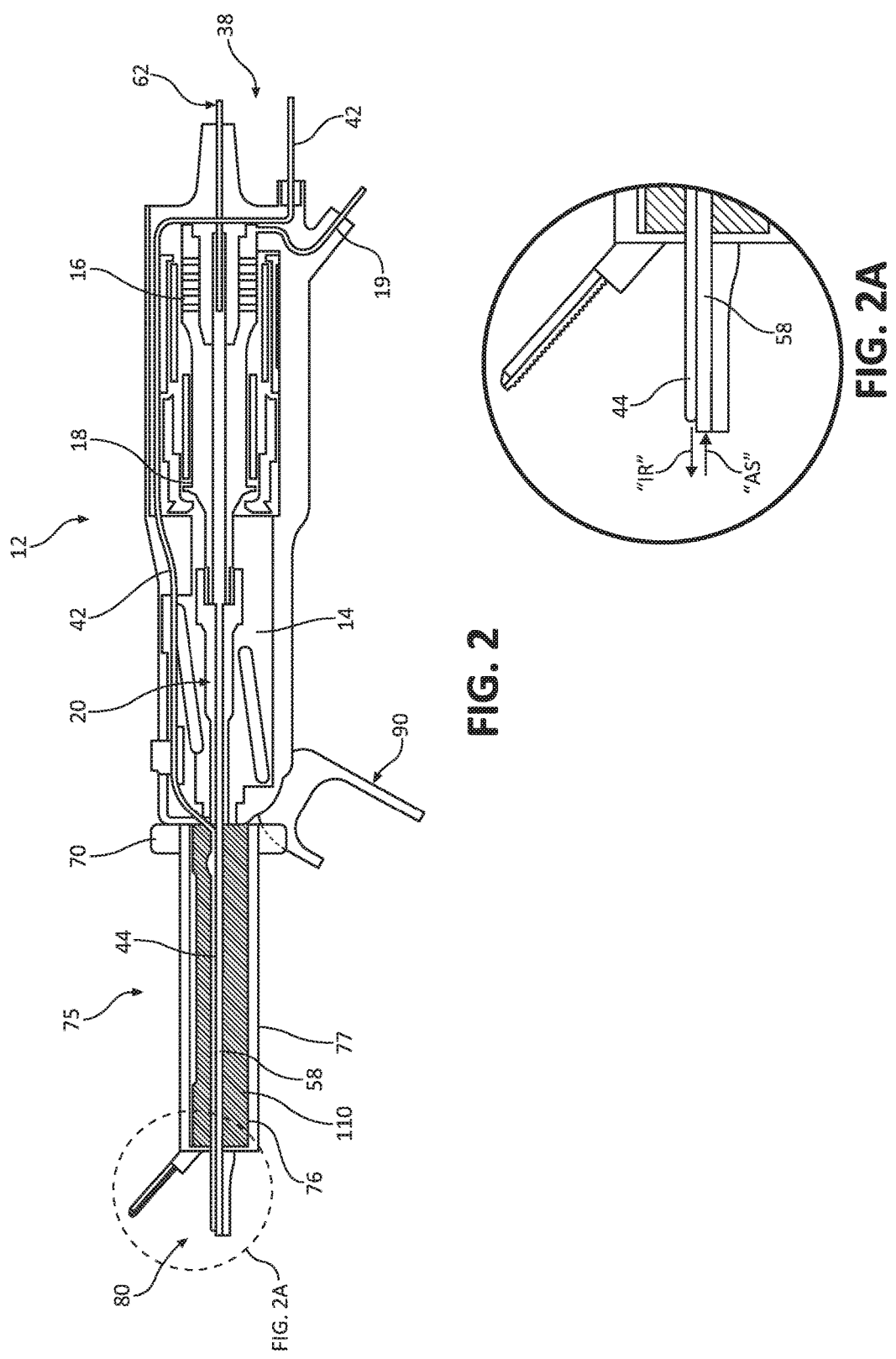

ULTRASONIC SURGICAL INSTRUMENT

BACKGROUND

1. Technical Field

The present disclosure relates to surgical instruments, and more particularly, to an ultrasonic surgical instrument configured to treat tissue with ultrasonic energy.

2. Discussion of Related Art

Ultrasonic devices for surgical uses are well known. Ultrasonic devices convert electrical energy into high frequency mechanical impulses (ultrasonic waves) that are then used to treat tissue.

One type of commonly used ultrasonic surgical device is an ultrasonic aspirator, which typically includes a handpiece, an elongated probe, and a vibrating tip. Ultrasonic waves emanating from the vibrating tip treat tissue with high water content (e.g., tumors, liver parenchyma) while tissue with low water content (e.g., nerves, vessels, membranes) is left untreated or minimally treated. Thus, ultrasonic aspirators demonstrate inherent tissue selectivity, providing the ability to avoid critical tissue structures from damage. Ultrasonic aspirators are useful for fine dissection of soft and calcified tissues such as liver parenchyma and soft tumors. However, ultrasonic aspirators have limited hemostatic effect and little ability to dissect other tissues, such as connective tissue. As a result, ultrasonic aspirators are often used with other surgical devices, e.g., ultrasonic shears.

Ultrasonic shears provide good hemostatic effect and are capable of dissecting connective tissue. Ultrasonic shears usually include an elongated shaft attached to a handle assembly. The distal end of the elongated shaft may have a blade and clamp mechanism capable of grasping, coagulating, and cutting tissue. However, ultrasonic shears may increase the risk of inadvertently grasping, coagulating, and cutting critical tissue structures. Thus, during certain procedures, surgeons often use both devices, leveraging the strength of each device. For example, in a liver transection, a surgeon may use an ultrasonic aspirator for fine dissection of liver parenchyma and then transition to ultrasonic shears to skeletonize and seal bile ducts. Using several devices during a procedure may be expensive, cumbersome, and increase operation time and complexity.

SUMMARY

Provided in accordance with aspects of the present disclosure is an ultrasonic surgical instrument including a handpiece, a lever operably coupled to the handpiece and movable between first, second, and third positions, a shaft assembly extending distally from the handpiece, and an ultrasonic waveguide extending through the shaft assembly and defining a fixed jaw member at a distal portion thereof. A movable jaw member may be disposed towards a distal portion of the shaft assembly and operably coupled to the lever such that movement of the lever between the first, second, and third positions moves the movable jaw member relative to the fixed jaw member between a retracted position, wherein the movable jaw member is retracted relative to the fixed jaw member, an extended open position, wherein the movable jaw member opposes and is spaced-apart from the fixed jaw member, and an extended closed position, wherein the movable jaw member opposes and is approximated relative to the fixed jaw member.

In an aspect of the present disclosure, the fixed jaw member defines a first aperture adapted to emit irrigation fluid therefrom.

In another aspect of the present disclosure, the first aperture communicates with a first passageway extending through the waveguide or the shaft assembly to the handpiece.

In yet another aspect of the present disclosure, the fixed jaw member defines a second aperture for receiving aspirated material from a surgical site.

In still another aspect of the present disclosure, the second aperture communicates with a second passageway extending through the waveguide or the shaft assembly to the handpiece.

In another aspect of the present disclosure, an ultrasonic transducer is disposed within the handpiece and operably coupled to the waveguide.

In yet another aspect of the present disclosure, a dual stage button is disposed on the handpiece and coupled to the ultrasonic transducer for activating the ultrasonic transducer in each of a low power mode and a high power mode.

In still another aspect of the present disclosure, a drive assembly is operably coupled between the movable jaw member and the lever such that movement of the lever between the first, second, and third positions moves the movable jaw member relative to the fixed jaw member between the retracted, extended open, and extended closed positions.

In still yet another aspect of the present disclosure, the drive assembly includes an actuation sleeve slidably disposed within the shaft assembly, the actuation sleeve having a proximal end portion operatively connected to the lever and a distal end portion operatively connected to the movable jaw member, wherein movement of the lever translates the actuation sleeve through the shaft assembly to move the movable jaw member relative to the fixed jaw member.

In another aspect of the present disclosure, an upper pin and a lower pin are operably associated with the movable jaw member.

In yet another aspect of the present disclosure, the shaft assembly defines a dual slot arrangement including an upper slot for receipt of the upper pin, the upper slot having a proximal longitudinal portion and a distal downward sloping portion, and a lower slot for receipt of the lower pin, the lower slot having a proximal longitudinal portion and a distal downward sloping portion.

In still yet another aspect of the present disclosure, in the retracted position of the movable jaw member, the upper and lower pins are disposed at proximal end portions of the proximal longitudinal portions of the respective upper and lower slots.

In still another aspect of the present disclosure, in the extended open position of the movable jaw member, the upper pin is disposed at a transition between the proximal longitudinal portion and the distal downward sloping portion of the upper slot, and the lower pin is disposed at a distal end of the distal downward sloping portion of the lower slot.

In another aspect of the present disclosure, in the extended closed position of the movable jaw member, the upper and lower pins are disposed at distal end portions of the distal downward sloping portions of the respective upper and lower slots.

In yet another aspect of the present disclosure, a dial is disposed at a distal end portion of the handpiece and operably coupled to the shaft assembly for selectively rotating the shaft assembly and the end effector assembly relative to the handpiece.

In still yet another aspect of the present disclosure, the handpiece includes a fluid inlet port configured to operably couple to a fluid source.

In still another aspect of the present disclosure, the handpiece includes a suction port configured to operably couple to a source of vacuum.

In another aspect of the present disclosure, the movable jaw member includes a clamp pad disposed thereon.

In yet another aspect of the present disclosure, the clamp pad further includes teeth configured to facilitate grasping tissue between the movable jaw member and the fixed jaw member.

BRIEF DESCRIPTION OF THE DRAWINGS

Objects and features of the present disclosure will become apparent to those of ordinary skill in the art when descriptions thereof are read with reference to the accompanying drawings, of which:

FIG. 2 is a side, longitudinal, cross-sectional view of the ultrasonic surgical instrument of FIG. 1;

FIG. 2A is an enlarged, cross-sectional view of the indicated area of detail delineated in FIG. 2;

DETAILED DESCRIPTION OF THE EMBODIMENTS

The ultrasonic surgical instrument of the present disclosure incorporates the features of ultrasonic aspirators and ultrasonic shears into a single device. In the ultrasonic aspiration mode, the device allows for fine dissection of tissue, for example, around critical structures. In the ultrasonic shears mode, the device provides the ability to clamp, coagulate, and/or dissect tissue. These and other aspects and features of the present disclosure are detailed hereinbelow.

Figure 1:
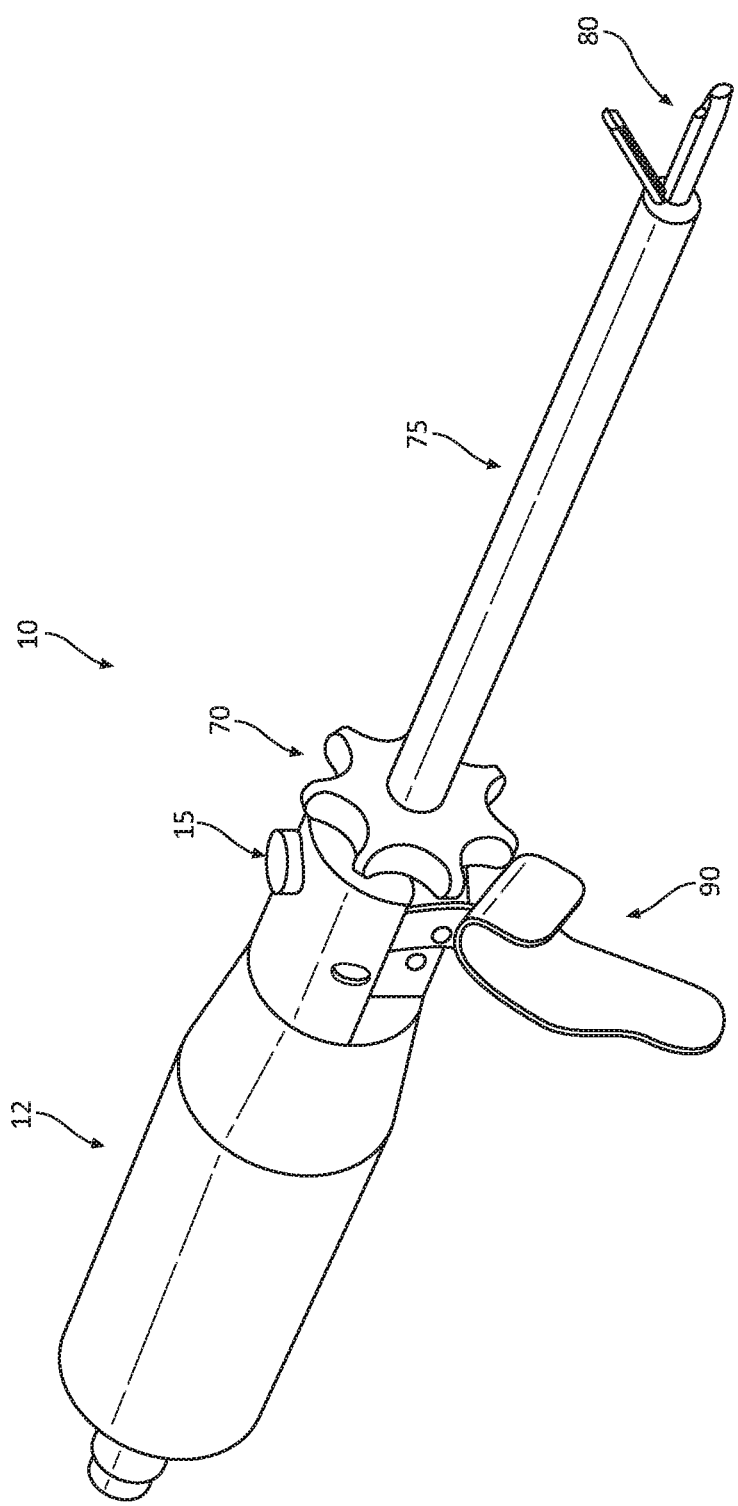
FIG. 1 is a perspective view of one illustrative embodiment of an ultrasonic surgical instrument provided in accordance with the present disclosure.
Figure 6:
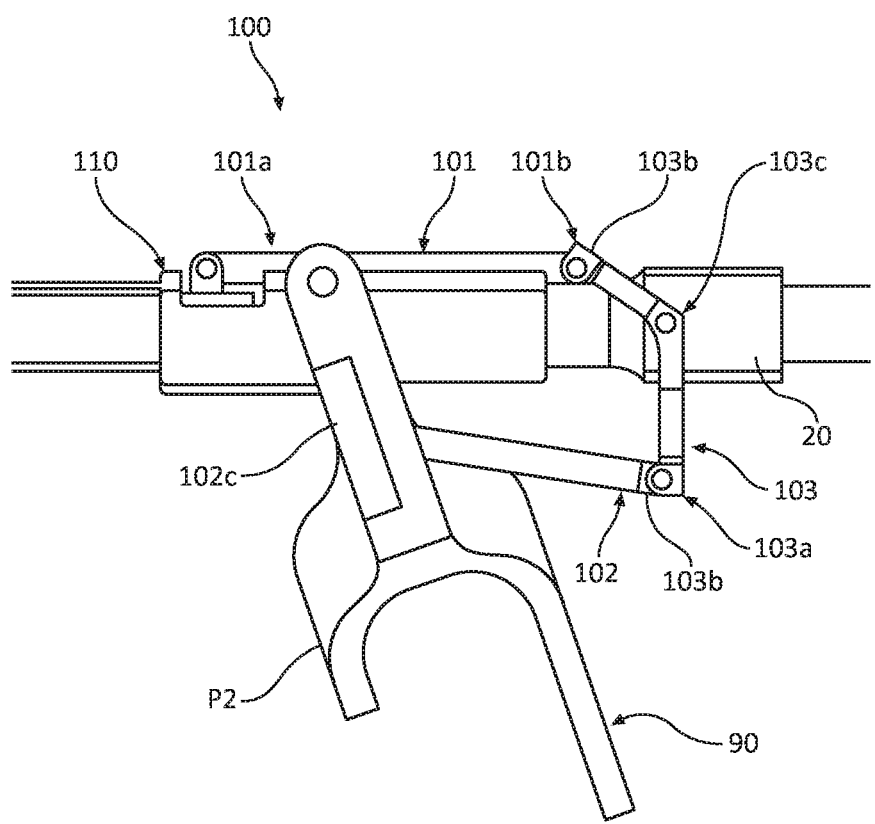
FIG. 6 is a side view of the drive assembly of the ultrasonic surgical instrument of FIG. 1.

Referring generally to FIG. 1, an ultrasonic surgical instrument 10 provided in accordance with the present disclosure generally includes a handpiece 12, a body assembly 14 (FIG. 2), a dual stage button 15, a dial 70, a shaft assembly 75, an end effector assembly 80, a lever 90, and a drive assembly 100 (FIG. 6). Aspects and features of ultrasonic surgical instrument 10 not germane to the understanding of the present disclosure are omitted to avoid obscuring the aspects and features of the present disclosure in unnecessary detail.

Referring to FIGS. 1, 2, and 2A, handpiece 12 at least partially encloses and supports a body assembly 14 including a transducer 16, e.g., a piezoelectric stack, a horn 18, and a waveguide 20 that extends distally from handpiece 12 to end effector assembly 80. A cable 19 electrically couples the transducer 16 to a source of electrical energy (not shown). In embodiments, an O-ring (not shown) may be placed onto the proximal end of the transducer. Electrical energy provided from the electrical energy source (not shown) is transmitted to electrodes associated with transducer 16 to drive the transducer 16. Transducer 16 converts the electrical energy into mechanical impulses (i.e., ultrasonic waves) which are then transmitted through horn 18 to waveguide 20. Transducer 16 is configured as a piezoelectric stack and may operate at a frequency of between 23 Hz to 55 kHz, although it is also envisioned that any suitable transducer of any frequency may be used. As will be described in further detail below (FIGS. 3A-5B), the resulting ultrasonic energy transmitted via waveguide 20 to end effector assembly 80 allows end effector assembly 80 to treat tissue. Dial 70 is operably coupled to body assembly 14 so as to enable selective rotation of shaft assembly 75 and end effector assembly 80 relative to handpiece 12.

Dual stage button 15 may be used to activate ultrasonic surgical instrument 10 in both an ultrasonic aspiration mode "A" (FIG. 3B) and an ultrasonic shears mode "B" (FIGS. 4B and 5B), as described in further detail below. In the ultrasonic aspiration mode "A" (FIG. 3B), upon a first depression of dual stage button 15, ultrasonic surgical instrument 10 may be activated in a low power mode, which may initiate a tissue selective algorithm, e.g., low suction, low amplitude/frequency, and duty cycling. Upon a second depression of dual stage button 15 in the ultrasonic aspiration mode "A" (FIG. 3B), ultrasonic surgical instrument 10 may transition from the low power mode to a high power mode, corresponding to a debulking algorithm, e.g., high suction, high amplitude, no duty cycling. In the ultrasonic shears mode "B" (FIGS. 4B and 5B), the first and second depressions of dual stage button 15 may correspond to low and high power modes, respectively. In either mode, upon depression of dual stage button 15, ultrasonic energy is emitted from transducer 16 and transmitted along horn 18 and waveguide 20 to a fixed jaw member 83 defined at a distal end portion of waveguide 20. The ultrasonic energy causes fixed jaw member 83 of waveguide 20 to rapidly vibrate such that, when contacted with tissue, enables the treatment of tissue.

An irrigation and aspiration fluid housing 38 is disposed towards the proximal end portion of handpiece 12. A fluid inlet 42 communicates with an annular fluid line 44 defined between an inner surface of inner tube 76 of shaft assembly 75 and an outer surface of waveguide 20. Fluid line 44 ultimately communicates with an irrigation channel 82b (FIG. 3B) defined through body portion 82a (FIG. 3B) of fixed jaw member 83. Thus, irrigation fluid may be urged through fluid inlet 42, through annular fluid line 44, through body portion 82a of fixed jaw member 83, and out a distal opening 82c of irrigation channel 82b, as indicated by arrow "IR" (FIG. 2A). Outer tube 77 of shaft assembly 75 surrounds inner tube 76, with actuation shaft 110 of drive assembly 100 (FIGS. 2 and 6) disposed therebetween. Irrigation channel 82b may include a polyimide tube (not shown) extending at least partially therethrough. Further, a flue (not shown) of any suitable shape, size, or material may be placed around distal opening 82c.

An aspiration channel 81b extends longitudinally from a distal opening 81c defined within body portion 81a of fixed jaw member 83 to an axial passage 58 defined within waveguide 20. An outlet conduit 62 communicates with axial passage 58 to enable the aspiration of irrigation fluid and emulsified tissue adjacent to end effector assembly 80. Fluid inlet 42 and outlet conduit 62 may be coupled separately to a pump source (not shown) and a vacuum source (not shown), respectively, for enabling irrigation and aspiration, or may be coupled to a combined pump/vacuum source (not shown). Thus, emulsified tissue and irrigation fluid may be aspirated, e.g., vacuumed or pumped, as indicated by arrow "AS" (FIG. 2A), into distal opening 81c and aspiration channel 81b through axial passage 58 and out of outlet conduit 62.

Shaft assembly 75 extends distally from handpiece 12 and includes end effector assembly 80 (FIGS. 1-5) disposed at a distal end portion thereof. Outer tube 77 of shaft assembly 75 defines a slot arrangement 120 (FIGS. 3B, 4B, 5B) towards the distal end portion thereof. End effector 80 includes fixed jaw member 83 defined at the distal end portion of waveguide 20 and a movable jaw member 84. Movable jaw member 84 includes a body 84a and two pins 84b, 84c operably coupled to body 84a, which are engagable and/or movable within slot arrangement 120 (FIGS. 3B-5B), as detailed below, to manipulate movable jaw member 84 relative to fixed jaw member 83.

Movable jaw member 84 defines a jaw member body 84a and two pins disposed thereon: an upper pin 84b and a lower pin 84c. Upper pin 84b and lower pin 84c, in relation to each other, may be configured in a longitudinally offset arrangement. Movable jaw member 84 is slidably and pivotably mounted relative to fixed jaw member 83 and shaft assembly 75 via receipt of pins 84b, 84c within slot arrangement 120 of shaft assembly 75. As will be described below, in addition to the ultrasonic aspiration mode "A" (FIGS. 3A and 3B) in which fixed jaw member 83 is utilized to treat, e.g., dissect, tissue, fixed jaw member 83 may be used in conjunction with movable jaw member 84 in an ultrasonic shears mode "B" (FIGS. 4A-4B) to selectively grasp and treat, e.g., coagulate and dissect tissue.

Movable jaw member 84 may include a clamp pad 85 (FIG. 4B) disposed thereon. Claim pad 85 may define teeth 86 (FIG. 4B) to provide traction against movement of tissue disposed between jaw members 83, 84. Clamp pad 85 (FIG. 4B) may also include tread patterns or other suitable patterns for this purpose, and may be formed from TEFLON™ or the like to reduce friction. Fixed jaw member 83 may have a Gaussian cross-sectional profile or other suitable cross-sectional profile to provide the best surface area for distribution of ultrasonic energy and for adequate tissue contact. In addition, the Gaussian cross-sectional profile maximizes displacement with minimal stress. Body portion 82a of fixed jaw member 83 provides a sharp edge, e.g., for the dissection and sealing of tissue.

Figure 3A:
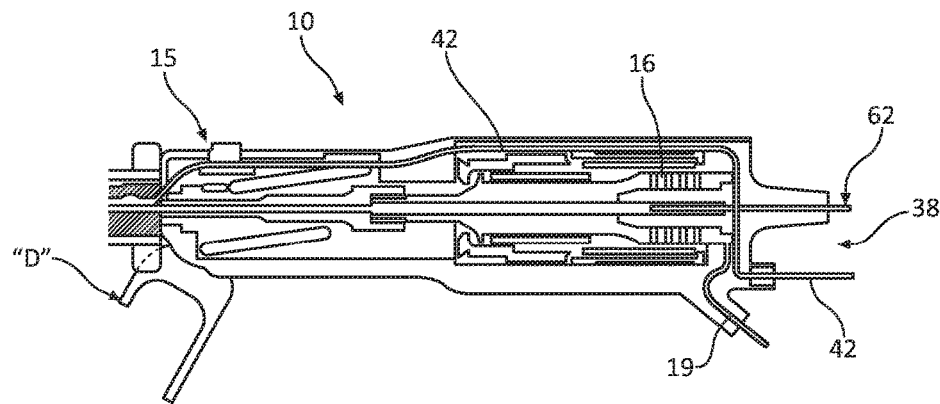
FIG. 3A is a side, longitudinal, cross-sectional view of a proximal end portion of the ultrasonic surgical instrument of FIG. 1 showing a lever in a distal position "D"
Figure 3B:
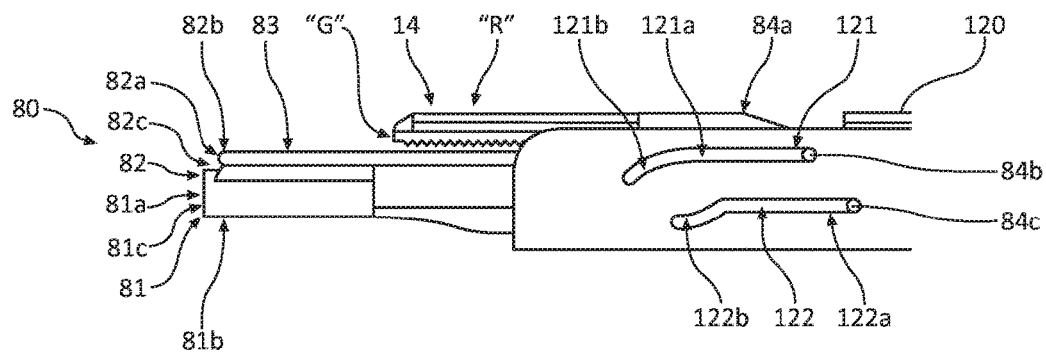
FIG. 3B is a side view of an end effector assembly of the ultrasonic surgical instrument of FIG. 1 in a retracted position "R" corresponding to the distal position "D" of the lever.

Referring to FIGS. 1, 2, and 6, lever 90 is disposed on and extends into handpiece 12. Lever 90 is movable between a distal position "D" (FIG. 3A), a first proximal position "P1" (FIG. 4A), and a second proximal position "P2" (FIG. 5A) and is operably connected to drive assembly 100 (FIG. 6). Drive assembly 100 includes an actuation shaft 110 that extends between inner tube 76 and outer tube 77 of shaft assembly 75 and is operably coupled to jaw member 84. As detailed below, movement of lever 90 translates actuation shaft 110 to move movable jaw member 84. The retention of pins 84b, 84c within slot arrangement 120 allows movable jaw member 84 to be movable between a retracted position "R" (FIG. 3B), an open position "O" (FIG. 4B), and/or closed position "C" (FIG. 5B) in response to movement of lever 90. When movable jaw member 84 is in the retracted position "R" (FIG. 3B), ultrasonic surgical instrument 10 is in the "ultrasonic aspiration mode "A" (FIGS. 3A and 3B). When jaw member 84 is in the open position "O" or closed position "C" (FIGS. 4B and 5B, respectively), ultrasonic surgical instrument 10 is in the ultrasonic shears mode "B" (FIGS. 4A-5B) and can be utilized in conjunction with fixed jaw member 83 to enable the selective grasping, coagulation, and dissection of tissue.

With particular reference to FIG. 6, drive assembly 100 generally includes, in addition to actuation shaft 110, an upper bar 101, a lower bar 102, and a cross bar 103 disposed between upper and lower bars 101, 102 and interconnecting upper and lower bars 101, 102. A distal end portion 102a of lower bar 102 is operatively connected to lever 90 while a proximal end portion 102b of lower bar 102 is operatively connected, e.g., pivotably coupled, to a lower end 103a of cross bar 103. A proximal end portion 101b of upper bar 101 is operatively connected, e.g., pivotably coupled, to an upper end 103b of cross bar 103, while a distal end portion 101a of upper bar 101 is operatively connected, e.g., pivotably coupled, to actuation shaft 110. A middle portion 103c of cross bar 103 is operatively connected, e.g., pivotably coupled, to body assembly 14. Actuation shaft 110 is slidably mounted relative to handpiece 12 and shaft assembly 75 for movement in an axial direction (e.g., distally and proximally).

Lever 90 extends into and is pivotably coupled within handpiece 12 to enable lever 90 to pivot upon a fixed point within handpiece 12 between the three positions described above ("D," "P1," and "P2," (FIGS. 3B, 4B, 5B, respectively)). Since lever 90 is operatively connected to drive assembly 100, which is operatively connected to actuation shaft 110, movement of lever 90 urges actuation shaft 110 distally or proximally in the axial direction depending on the position of lever 90. More specifically, pivoting of lever 90 distally urges actuation shaft 110 proximally, while pivoting of lever 90 proximally urges actuation shaft 110 distally. A distal end portion of actuation shaft 110 (FIG. 2) is operatively connected to movable jaw member 84.

Referring back to FIGS. 3A-5B, slot arrangement 120 includes an upper slot 121 and a lower slot 122 defined within outer tube 77 of shaft assembly 75. Upper slot 121 has a longitudinal portion 121a that transitions into a downward sloping distal portion 121b. Lower slot 122 has a longitudinal portion 122a that transitions into a downward sloping distal portion 122b. Distal portion 121b and/or distal portion 122b may be linear or may define curved configurations. Upper pin 84b of movable jaw member 84 is slidably disposed within upper slot 121, while lower pin 84c of movable jaw member 84 is slidably disposed within lower slot 122. The relative positioning of pins 84b, 84c on movable jaw member 84 and the configuration and relative positioning of slots 121, 122 provides a configuration whereby pivoting of lever 90 moves movable jaw member 84 between its three positions, as detailed below. Although ultrasonic surgical instrument 10 is shown as a "pencil-style" device, it should be appreciated that ultrasonic surgical instrument 10 could be implemented with a pistol grip or any other suitable configuration. Ultrasonic surgical instrument 10 may also be operatively connected to a computing device (not shown), such that the operation of ultrasonic surgical instrument 10 may be monitored and/or adjusted before or during a procedure. Ultrasonic surgical instrument 10 may also be provided in a battery powered and/or cordless configuration.

Referring now to FIGS. 3A and 3B, ultrasonic surgical instrument 10 is shown in the ultrasonic aspiration mode "A." The ultrasonic aspiration mode "A" is achieved when lever 90 is moved to a distal most position "D." In ultrasonic aspiration mode "A," end effector 80 of ultrasonic surgical instrument 10 may be used, for example, to finely/precisely dissect tissues around critical structures.

In ultrasonic aspiration mode "A," jaw member 84 is in a retracted position "R" such that it does not obstruct the surgeon's view during a procedure or interfere with fine dissection of tissue. Suction and/or irrigation are operable in the ultrasonic aspiration mode "A." For example, irrigation fluid is ejected from distal opening 82c of irrigation channel 82b to wash the transection plane and tissue particles from the surgical site such that the surgeon's view remains unobstructed. Additionally, irrigation fluid from distal opening 82c of irrigation channel 82b may cool fixed jaw member 83 to prevent burning or charring of tissue. Fluid flowing into and through ultrasonic surgical instrument 10 may also prevent ultrasonic surgical instrument 10 from failure caused by overheating. Likewise, fragmented bits of tissue as well as irrigation fluid and other fluids are aspirated from the surgical site through distal opening 81c of aspiration channel 81b. Distal openings 81c, 82c may have a substantially teardrop shape to facilitate, e.g., the aspiration and irrigation of tissue.

As shown in FIG. 3B, with movable jaw member 84 in the retracted position "R," upper pin 84b and lower pin 84c are disposed at the most proximal ends of upper slot 121 and lower slot 122, respectively. In this retracted position "R," clamp pad 85 of jaw member 84 is not in contact with jaw member 83 as shown by gap "G" (FIG. 3B).

Figure 4A:
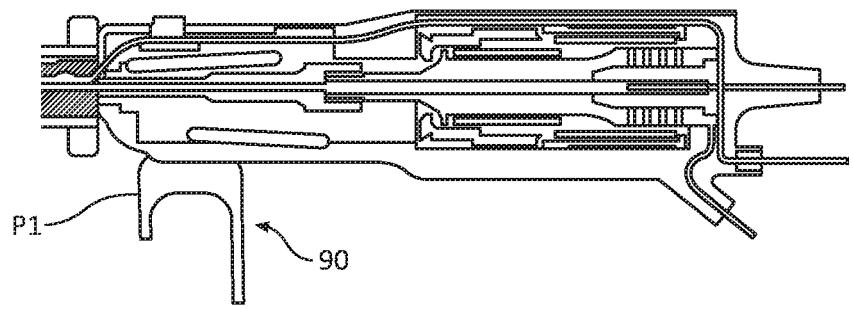
FIG. 4A is a side, longitudinal, cross-sectional view of the proximal end portion of the ultrasonic surgical instrument of FIG. 1 showing the lever in a first proximal position "P1"
Figure 4B:
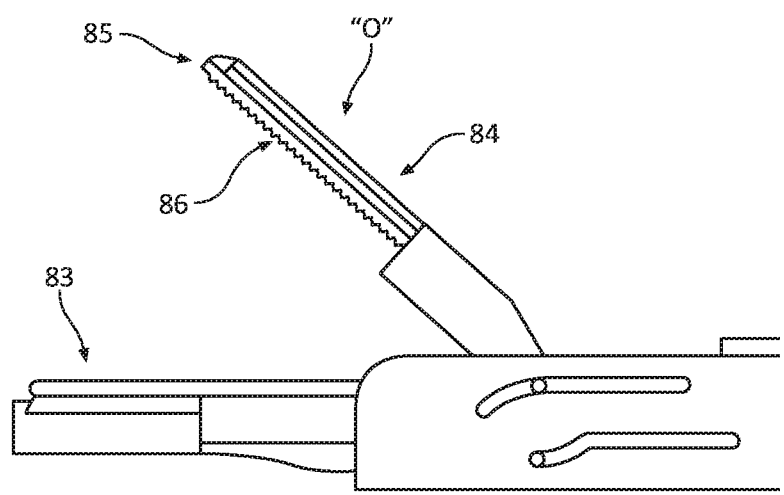
FIG. 4B is a side view of the end effector assembly of the ultrasonic surgical instrument of FIG. 1 in the open position "O" corresponding to the first proximal position "P1" of the lever.
Figure 5A:
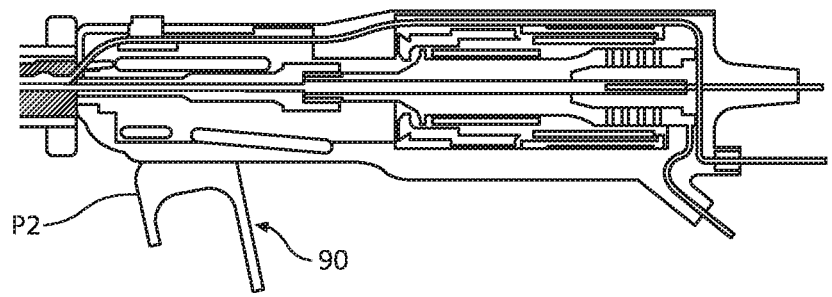
FIG. 5A is a side, longitudinal, cross-sectional view of the proximal end portion of the ultrasonic surgical instrument of FIG. 1 showing the lever in a second proximal position "P2"
Figure 5B:
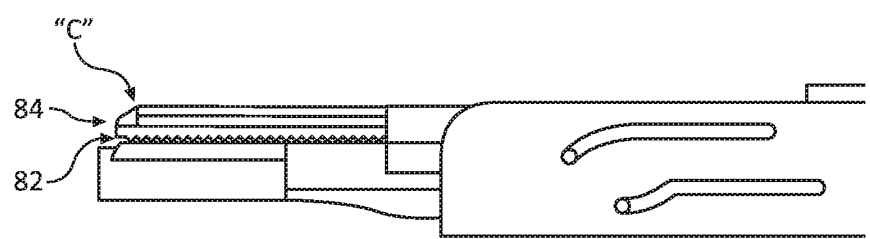
FIG. 5B is a side view of the end effector assembly of the ultrasonic surgical instrument of FIG. 1 in a closed position "C" corresponding to the second proximal position "P2" of the lever.

Referring now to FIGS. 4A and 4B, ultrasonic surgical instrument 10 is shown in the ultrasonic shears mode "B." In the ultrasonic shears mode "B," ultrasonic surgical instrument 10 can be used to treat (e.g., coagulate and/or dissect) tissue. The ultrasonic shears mode "B" may be achieved when lever 90 is moved from the distal position "D" (FIG. 3A) to a first proximal position "P1" (FIG. 4A), which causes movable jaw member 84 to extend and pivot from the retracted position "R" (FIG. 3B) to the extended, open position "O" (FIG. 4B). As shown in FIG. 5A, further proximal movement of lever 90 causes it to reach its proximal most position, or second proximal position "P2," which causes jaw member 84 to pivot towards jaw member 83 into a closed position "C" (FIG. 5B). Thus, in ultrasonic shears mode "B," tissue disposed between jaw members 83, 84 can be grasped and treated.

In order to move movable jaw member 84 from the retracted position "R" (FIG. 3B) to the extended, open position "O" (FIG. 4B), as noted above, lever 90 is pivoted proximally from the distal position "D" to the first proximal position "P1." In response to this movement of lever 90, actuation shaft 110 (FIGS. 2 and 6) is moved distally such that lower pin 84c of jaw member 84 is moved to the most distal position of distal portion 122b of lower slot 122, while upper pin 84b is moved to the transition point between longitudinal portion 121a and distal portion 121b of slot 121. This movement of pins 84b, 84c within slots 121, 122 guides movable jaw member 84 to move distally and pivot to the extended, open position "O," whereby lower pin 84c in the distal most position of distal portion 122b of lower slot 122 acts as a pivot point for jaw member 84. In open position "O," upper pin 84b and lower pin 84c may be longitudinally aligned, as shown in FIG. 4B.

Referring to FIGS. 5A and 5B, in order to pivot movable jaw member 84 from the open position "O" (FIG. 4B) to the closed position "C" (FIG. 5B), as noted above, lever 90 is pivoted proximally from the first proximal position "P1" (FIG. 4A) to the second proximal position "P2" (FIG. 5A). In response to this movement of lever 90, actuation shaft 110 (FIGS. 2 and 6) is moved further distally such that upper pin 84b and lower pin 84c of jaw member 84 are guided into the distal most position of distal portion 121b of upper slot 121 and the distal most position of distal portion 122b of lower slot 122, respectively. To achieve the closed position "C," upper pin 84b and lower pin 84c of jaw member body 84a and jaw member 84 are urged distally and through the downwardly sloping distal portions 121b, 122b of slots 121, 122, causing clamp pad 85 of jaw member 84 to contact and engage with jaw member 83, thereby eliminating gap "G." However, it is also contemplated that, rather than entirely eliminating the gap "G," a smaller gap be provided in the closed position "C".

The travel distance of jaw member 84 between the retracted position "R," open position "O," and/or closed position "C" may be relatively small. To give a user appropriate tactile feedback between the actuation of lever 90 and the resulting travel of jaw member 84 within slot arrangement 120, the boomerang-shape-like configuration of cross bar 103 allows for maximum travel of lever 90, such that the travel of lever 90 from each position (e.g., "D" to "P1" or "D to "P2," "P1" to "D" or "P1" to "P2," "P2" to "D" or "P2" to "P1") is amplified versus the actual travel distance of jaw member 84, resulting in an appropriate level of tactile feedback.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawings are presented only to demonstrate certain examples of the disclosure. Other elements, steps, methods, and techniques that are insubstantially different from those described above and/or in the appended claims are also intended to be within the scope of the disclosure.

What is claimed is:
1. An ultrasonic surgical instrument, comprising:
    a handpiece;
    a lever operably coupled to the handpiece and movable between first, second, and third positions;
    a shaft assembly extending distally from the handpiece;
    an ultrasonic waveguide extending through the shaft assembly and defining a fixed jaw member at a distal portion thereof;
    a movable jaw member disposed towards a distal portion of the shaft assembly and operably coupled to the lever such that movement of the lever between the first, second, and third positions moves the movable jaw member relative to the fixed jaw member between a retracted position, wherein the movable jaw member is retracted relative to the fixed jaw member, an extended open position, wherein the movable jaw member opposes and is spaced-apart from the fixed jaw member, and an extended closed position, wherein the movable jaw member opposes and is approximated relative to the fixed jaw member.

2. The ultrasonic surgical instrument of claim 1, wherein the fixed jaw member defines a first aperture adapted to emit irrigation fluid therefrom.

3. The ultrasonic surgical instrument of claim 2, wherein the first aperture communicates with a first passageway extending through the waveguide or the shaft assembly to the handpiece.

4. The ultrasonic surgical instrument of claim 1, wherein the fixed jaw member defines a second aperture for receiving aspirated material from a surgical site.

5. The ultrasonic surgical instrument of claim 4, wherein the second aperture communicates with a second passageway extending through the waveguide or the shaft assembly to the handpiece.

6. The ultrasonic surgical instrument of claim 1, further comprising an ultrasonic transducer disposed within the handpiece and operably coupled to the waveguide.

7. The ultrasonic surgical instrument of claim 6, further comprising a dual stage button disposed on the handpiece and coupled to the ultrasonic transducer for activating the ultrasonic transducer in each of a low power mode and a high power mode.

8. The ultrasonic surgical instrument of claim 1, further comprising a drive assembly operably coupled between the movable jaw member and the lever such that movement of the lever between the first, second, and third positions moves the movable jaw member relative to the fixed jaw member between the retracted, extended open, and extended closed positions.

9. The ultrasonic surgical instrument of claim 8, wherein the drive assembly includes an actuation shaft slidably disposed within the shaft assembly, the actuation shaft having a proximal end portion operatively connected to the lever and a distal end portion operatively connected to the movable jaw member, wherein movement of the lever translates the actuation shaft through the shaft assembly to move the movable jaw member relative to the fixed jaw member.

10. The ultrasonic surgical instrument of claim 1, further comprising an upper pin and a lower pin operably associated with the movable jaw member.

11. The ultrasonic surgical instrument of claim 10, wherein the shaft assembly defines a dual slot arrangement including:

an upper slot for receipt of the upper pin, the upper slot having a proximal longitudinal portion and a distal downward sloping portion; and a lower slot for receipt of the lower pin, the lower slot having a proximal longitudinal portion and a distal downward sloping portion.

12. The ultrasonic surgical instrument of claim 11, wherein, in the retracted position of the movable jaw member, the upper and lower pins are disposed at proximal end portions of the proximal longitudinal portions of the respective upper and lower slots.

13. The ultrasonic surgical instrument according to claim 11, wherein, in the extended open position of the movable jaw member, the upper pin is disposed at a transition between the proximal longitudinal portion and the distal downward sloping portion of the upper slot, and the lower pin is disposed at a distal end of the distal downward sloping portion of the lower slot.

14. The ultrasonic surgical instrument according to claim 11, wherein, in the extended closed position of the movable jaw member, the upper and lower pins are disposed at distal end portions of the distal downward sloping portions of the respective upper and lower slots.

15. The ultrasonic surgical instrument of claim 1, further comprising a dial disposed at a distal end portion of the handpiece and operably coupled to the shaft assembly for selectively rotating the shaft assembly and the end effector assembly relative to the handpiece.

16. The ultrasonic surgical instrument of claim 1, wherein the handpiece further comprises a fluid inlet port configured to operably couple to a fluid source.

17. The ultrasonic surgical instrument of claim 1, wherein the handpiece further comprises a suction port configured to operably couple to a source of vacuum.

18. The ultrasonic surgical instrument of claim 1, wherein the movable jaw member further comprises a clamp pad disposed thereon.

19. The ultrasonic surgical instrument of claim 18, wherein the clamp pad further comprises teeth configured to facilitate grasping tissue between the movable jaw member and the fixed jaw member.

20. The ultrasonic surgical instrument of claim 4, wherein the first aperture and the second aperture have a substantially teardrop shape to facilitate irrigation and aspiration of tissue.

* * * * *